(12) United States Patent
Crutcher et al.

(10) Patent No.: US 6,245,751 B1
(45) Date of Patent: *Jun. 12, 2001

(54) METHODS FOR THE TREATMENT OF APOLIPOPROTEIN E RELATED DISEASES

(75) Inventors: Keith A. Crutcher; Judith A. K. Harmony, both of Cincinnati, OH (US)

(73) Assignee: University of Cincinnati, Cincinnati, OH (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/214,742

(22) PCT Filed: Jul. 8, 1997

(86) PCT No.: PCT/US97/11836

§ 371 Date: Sep. 10, 1999

§ 102(e) Date: Sep. 10, 1999

(87) PCT Pub. No.: WO98/01101

PCT Pub. Date: Jan. 15, 1998

Related U.S. Application Data

(60) Provisional application No. 60/021,405, filed on Jul. 9, 1996.

(51) Int. Cl.$^7$ .......................... A61K 31/715; A61K 31/70; A01N 43/04

(52) U.S. Cl. ................................ 514/54; 514/56; 514/59; 514/62

(58) Field of Search ................................ 514/54, 56, 59, 514/62

(56) References Cited

U.S. PATENT DOCUMENTS

| | | |
|---|---|---|
| 3,000,787 | 9/1961 | Bianchini et al. . |
| 3,454,560 | 7/1969 | Nagasawa et al. . |
| 4,727,063 | 2/1988 | Naggi et al. . |
| 4,956,347 | 9/1990 | Ban et al. . |
| 5,164,295 | 11/1992 | Kisilevsky et al. . |
| 5,384,398 | 1/1995 | Lormeau et al. . |
| 5,508,167 | 4/1996 | Roses et al. . |
| 5,795,860 | 8/1998 | Witt et al. . |

OTHER PUBLICATIONS

Adams et al., "Degenerative Diseases Of The Nervous System In The Aged," *Principles of Neurology*, Ch. 25, pp. 401–407 (1977).

Baraitser, *The Genetics of Neurological Disorders*, 2nd edition, pp. 85–88 (1990).

Caputo, C.B., "What is the Significance of the Binding of Proteoglycans to Amyloid?," *Neurobiology of Aging* 10:503–504 (1989).

Cardin, A.D. et al., "Binding Of A High Reactive Heparin To Human Apolipoprotein E: Identification Of Two Heparin–Binding Domains," *Biochemical and Biophysical* 134(2):783–789 (1986).

Cardin, A.D. et al., "Dependence on heparin chain–length of the interaction of heparin with human plasma low density lipoproteins," *Int. J. Biol. Macromol.* 11:59–62 (1989).

Clay, M.A. et al., "Localization of a Domain in Apolipoprotein E with both Cytostatic and Cytotoxic," *Biochemistry* 34:11142–11151 (1995).

Crutcher, K.A. et al., "Neurite Degeneration Elicited by Apolipoprotein E Peptides," *Experimental Neurology* 130:120–126 (1994).

Curtiss, L.K. et al., "Cord Blood Plasma Lipoproteins Inhibit Mitogen–Stimulated Lymphocyte Proliferation," *J. Immunol.* 133(3):1379–1384 (1984).

Deng, J. et al. "Lysosomal degradation and sorting of apolipoprotein E in macrophages," *Journal of Lipid Research* 36:2129–2140 (1995).

Dyer, C.A. et al., "Structural features of synthetic peptides of apolipoprotein E that bind the LDL receptor," *Journal of Lipid Research* 36:80–88 (1995).

Dyer, C.A. et al., "Apoprotein E–rich High Density Lipoprotein Inhibit Ovarian Androgen Synthesis," *J. Biol. Chem.* 263(22):10965–10973 (1988).

Dyer, C.A. et al., "Only Multimers of a Synthetic Peptide of Human Apolipoprotein E Are Biologically Active," *J. Biol. Chem.* 266(23):15009–15015 (1991).

Dyer, C.A. et al., "A Synthetic Peptide Mimic Of Plasma Apolipoprotein E That Binds The LDL Receptor," *J. Biol. Chem.* 266(34):22803–22806 (1991).

Evans, D. et al., "Prevalence of Alzheimer's Disease in a Community Population of Older Persons," *JAMA* 262(18):2551–2556 (1989).

Fernandez, F. et al., "The haemorrhagic and antithrombotic effects of dermatan sulphate," *British Journal of Haematology* 64:309–317 (1986).

Forsyth, E. et al., "An Overview of the Etiology, Diagnosis, and Treatment of Alzheimer Disease," *Physical Therapy* 78(12):1325–1331 (1998).

Gilroy et al., "Degenerative Diseases Of The Nervous System," *Medical Neurology*, MacMillan Publishing Co., Ch. 4, pp. 175–179 (1979).

Hay, J.W. et al., "The Economic Costs Of Alzheimer's Disease," *Am. J. Public Health* 77(9):1169–1175 (1987).

(List continued on next page.)

*Primary Examiner*—William R. A. Jarvis
*Assistant Examiner*—Vickie Kim

(57) ABSTRACT

Methods for treating diseases associated with toxicity of Apolipoprotein E ("apoE"). Specifically, the present invention relates to new methods for treating a mammal having a condition associated with toxicity of apolipoprotein E cleavage fragments containing residues 130–169, comprising administering to said mammal a pharmacologically effective amount of compound or a pharmaceutically acceptable sale, derivative or fragment thereof to interfere with generation of toxic fragments of apolipoprotein E or with the receptor-binding site associated with residues 130–169 of the apolipoprotein E molecule in said mammal.

20 Claims, No Drawings

OTHER PUBLICATIONS

Hui, D.Y. et al., "Defective Hepatic Lipoprotein Receptor Binding Of β–Very Low Density Lipoproteins From Type III Hyperlipoproteinemic Patients," *J. Biol. Chem.* 259(2):860–869 (1984).

Kisilevsky, R. et al., "Arresting amyloidosis in vivo using small–molecule anionic sulphonates or sulphates: implications for Alzheimer's disease," *Nature Medicine* 1(2):143–148 (1995).

LaDu, M.J. et al., "Isoform–specific Binding of Apolipoprotein E to β–Amyloid," *J. Biol. Chem.* 269(38):23403–23406 (1994).

LaDu, M.J. et al., "Purification of Apolipoprotein E Attenuates Isoform–specific Binding to β–Amyloid," *J. Biol. Chem.* 270(6):9039–9042 (1995).

Lambert, J. et al., "A new polymorphism in the APOE promoter associated with risk of developing Alzheimer's Disease," *Human Molecular Genetics* 7(3):533–540 (1998).

Lambert, J. et al., "Pronounced impact of Th1/E47cs mutation compared with –491 AT mutation on neural APOE gene expression and risk of developing Alzheimer's disease," *Human Molecular Genetics* 7(9):1511–1516 (1998).

Leveugle, B. et al., "Binding of heparan sulfate glycosaminoglycan to β–amyloid peptide: inhibition by potentially therapeutic polysulfated compounds," *NeuroReport* 5(11):1389–1392 (1994).

Mahley, R.W. et al., "Plasma lipoproteins: apolipoprotein structure and function," *J. Lipid Research* 25:1277–1294 (1984).

Mahley, R.W., "Apolipoprotein E: Cholesterol Transport Protein With Expanding Role in Cell Biology," *Science* 240:622–630 (1988).

Margolis, R.U. et al., "Properties of Nervous Tissue Proteoglycans Relevant To Studies On Alzheimer's Disease," *Neurobiology of Aging* 10(1):500–502 (1989).

Marques, M.A. et al., "A thrombin cleavage fragment of apolipoprotein E exhibits isoform–specific neurotoxicity," *NeuroReport* 7(15):2529–2532 (1996).

Merritt, *A Textbook Of Neurology*, 6th edition, pp. 484–489, Lea & Febiger, Philadelphia (1979).

Mistry, M.J. et al., "Apolipoprotein E Restricts Interleukin–Dependent T Lymphocyte Proliferation at the $G1_A/G1_B$ Boundary," *Cellular Immunology* 160:14–23 (1995).

Navia, J.L. et al., "Assay of N–Acetylhaparosan Deacetylase with a Capsular Polysaccharide from *Escherichia coli* K5 as Substrate," *Analytical Biochemistry* 135:134–140 (1983).

Shelburne, F. et al., "Effect of Apoproteins on Hepatic Uptake of Triglyceride Emulsions in the Rat," *J. Clin. Invest.* 65:652–658 (1980).

Snow, A.D. et al., "Temporal Relationship between Glycosaminoglycan Accumulation and Amyloid Deposition during Experimental Amyloidosis," *Laboratory Investigation* 53(1):37–44 (1985).

Snow, A.D. et al., "The Presence of Heparan Sulfate Proteoglycans in the Neuritic Plagues and Congophilic Angiopathy in Alzheimer's Disease," *American Journal of Pathology* 133(3):456–463 (1988).

Stuhlsatz, H.W. et al., "The Preparation Of Dermatan Sulphate," *The Methodology Of Connective Tissue Research*, Ch. 14, 137–146 (1976).

Tolar, M. et al., "Neurotoxicity of the 22 kDa Thrombin-Cleavage Fragment of Apolipoprotein E and Related Synthetic Peptides Is Receptor–Mediated," *J. Neuroscience* 17(15):5678–5686 (1997).

Vogel, T. et al., "Apolipoprotein E: A Potent Inhibitor of Endothelial and Tumor Cell Proliferation," *Journal of Cellular Biochemistry* 54:299–308 (1994).

Weisgraber, K.H. et al., "The Receptor–Binding Domain of Human Apolipoprotein E," *J. Biol. Chem.* 258(20):12348–12354 (1983).

Wilson, C. et al., "Three–Dimensional Structure of the LDL Receptor–Binding Domain of Human Apolipoprotein E," *Science* 252:1817–1822 (1991).

Ye, S.Q. et al., "Inhibition of Apolipoprotein E Degradation in a Post–Golgi Compartment by a Cysteine Protease Inhibitor," *J. Biol. Chem.* 8497–8502 (1992).

Zannis, V.I. et al., "Proposed nomenclature of apoE isoproteins, apoE genotypes, and phenotypes," *J. Lipid Research* 23:911–914 (1982).

Cardin, A.D. et al., "Inhibition of Lymphocyte Proliferation By Synthetic Peptides Homologous To Human Plasma Apolipoproteins B and E," *Biochemical and Biophysical Research Communications* 154(2):741–745 (1988).

Cardin, A.D. et al., "Structural Properties Of The Heparin-Binding Domains Of Human Apolipoprotein E," *Adv. Exp. Med. Biol.* 243:157–163 (1988).

METHODS FOR THE TREATMENT OF APOLIPOPROTEIN E RELATED DISEASES

This application is 371 of PCT/US97/11836 filed Jul. 8, 1997 and also claims the benefit of Provisional No. 60/021,405 filed Jul. 9, 1996.

This U.S. Government has a paid-up license in this invention and the right in limited circumstances to require the patent owner to license others on reasonable terms as provided for by the terms of Grant No. RO1 HL27333 and NS31410 awarded by the National Institutes of Health.

BACKGROUND OF THE INVENTION

The present invention relates generally to a method for treating diseases associated with toxicity of Apolipoprotein E ("apoE"). Specifically, the present invention is a new method for treating a mammal having a condition associated with toxicity of apolipoprotein E cleavage fragments containing residues 130–169, comprising administering to said mammal a pharmacologically effective amount of compound or a pharmaceutically acceptable salt, derivative or fragment thereof to interfere with generation of the cleavage fragment or with the receptor-binding site associated with the cleavage fragment containing residues 130–169 of the apolipoprotein E molecule in said mammal.

Alzheimer's disease is the most common form of both senile and pre-senile dementia in the world and is recognized clinically as relentlessly progressive dementia that presents with increasing loss of memory, intellectual function and disturbances in speech (Merritt, 1979, *A Textbook of Neurology*,. 6th edition, pp. 484–489 Lea & Febiger, Philadelphia). The disease itself usually has a slow and insidious progress that affects both sexes equally, worldwide. It begins with mildly inappropriate behavior, uncritical statements, irritability, a tendency towards grandiosity, euphoria and deteriorating performance at work; it progresses through deterioration in operational judgment, loss of insight, depression and loss of recent memory; it ends in severe disorientation and confusion, apraxia of gait, generalized rigidity and incontinence (Gilroy & Meyer, 1979, *Medical Neurology*, pp.175–179 MacMillan Publishing Co.) Alzheimer's disease afflicts an estimated four million human beings in the United States alone at a cost of 35 billion dollars a year (Hay & Ernst, 1987, *Am. J. Public Health*, 77: 1169–1175). It is found in 10% of the population over the age of 65 and 47% of the population over the age of 85 (Evans et al., 1989, JAMA, 262:2551–2556). In addition, the disease is found at much lower levels in the younger age groups, usually beginning at about 30 years of age and even rarely in late childhood (Adams & Victor, 1977, *Principles of Neurology*, pp. 401–407).

The etiology of Alzheimer's disease is unknown. Evidence for a genetic contribution comes from several important observations such as the familial incidence, pedigree analysis, monozygotic and dizygotic twin studies and the association of the disease with Down's syndrome (for review see Baraitser, 1990, *The Genetics of Neurological Disorders*, 2nd edition, pp. 85–88). Nevertheless, this evidence is far from definitive and it is clear that one or more other factors are also required.

In recent years, research has suggested that apolipoprotein E ("apoE") plays a potential role in the pathogenesis of Alzheimer's disease. Apolipoprotein E performs various functions as a protein constituent of plasma lipoproteins, including its role in cholesterol metabolism. It was first identified as a constituent of liver-synthesized very low density lipoproteins ("VLDL") which function in the transport of triglycerides from the liver to peripheral tissues. ApoE is instrumental in lipoprotein metabolism in several ways. Mahley, et al., *J. Lipid Res.*, 25:1277–1294 (1984). It is a recognition site for several cellular lipoprotein receptors, including hepatocyte receptors for chylomicron and VLDL remnants Hui, et al., *J. Biol. Chem.*, 259:860–869 (1984); Shelburne, et al., *J. Clin. Invest.*, 65:652–658 (1980).

ApoE-enriched lipoproteins have also been described to have a function in the immune system by inhibiting mitogen-or antigen-stimulated lymphocyte proliferation in vitro and in vivo. In the ovary, apoE inhibits androgen production by LH-stimulated cultured theca and interstitial cells; Dyer, et al., *J. Biol. Chem.*, 263:10965 (1988).

Further substantiation that apoE and apoB-containing lipoproteins are important regulators of lymphocyte function has come from studies of the inhibitory properties of fetal cord blood plasma lipoproteins (Curtiss, et al., *J. Immunol.*, 133:1379 (1984)). In these studies a direct correlation between apoE and inhibition was established.

There are three major isoforms of ApoE, referred to as ApoE2, ApoE3 and ApoE4 which are products of three alleles at a single gene locus. Three homozygous phenotypes (Apo-E2/2, E3/3, and E4/4) and three heterozygous phenotypes (ApoE3/2, E4/3 and E4/2) arise from the expression of any two of the three alleles. The most common phenotype is ApoE3/3 and the most common allele is E3. See Mahley, R. W., *Science* 240:622–630(1988).

The amino acid sequences of the three types differ only slightly. ApoE4 differs from ApoE3 in that in ApoE4 arginine is substituted for the normally occurring cysteine at amino acid residue 112. The most common form of ApoE2 differs from ApoE3 at residue 158, where cysteine is substituted for the normally occurring arginine. See Mahley, *Science*, supra. ApoE phenotypes and genotypes are well described and known in the art as described above. The established nomenclature system as well as the phenotypes and genotypes for ApoE, are described in, for example, Zannis, et al., *J. Lipid. Res.* 23:911 et seq. (1982), which is incorporated by reference herein.

Subjects with the ApoE4/4 genotype are as much as eight times as likely to be affected by Alzheimer's disease as subjects with the ApoE2/3 or ApoE3/3 genotypes. Further, the average age of onset of Alzheimer's disease and the average age of survival is lower for those having one ApoE4 allele, and lowest for those having two ApoE4 alleles. Thus, a subjects prognosis for Alzheimer's disease is more likely to be negative if the subject has an ApoE4 allele and most negative if the subject has more than one ApoE4 allele. The negative prognosis can be viewed in terms of increased likelihood of developing the disease, or of dying at an earlier age. Other ApoE-linked diseases include type III Hyperlipidemia and atherosclerosis.

Studies have shown that apoE fragments ranging from 5 to 22 kD are present in the post-mortem cerebral spinal fluid from both control patients and patients with AD. The only major band immunoprecipitated by a monoclonal antibody that recognizes the putative toxic domain runs with an apparent molecular weight of about 22 kD. This fragment likely corresponds to the major thrombin cleavage product, which has been shown to be protease-resistant. Weisgraber, et al., *J. Biol. Chem.* 258:12348–54 (1983).

Amino acids 130–169 in human apoE encompass an immunoregulatory domain with both cytostatic and cytotoxic activities against IL2-dependent T cells. This finding is consistent with results of previous studies (Cardin, et al., 1988; Dyer, et al., 1991) that implicated residues 141–155 in apoE's antiproliferative effect on naive mitogen-activated T cells. The similar potencies of E130–149 and E130–155 indicate that the cytostatic domain is located within residues 130–149. However, a longer peptide representing residues 130–169 and dimeric peptides of amino acids 141–155 also have potent cytotoxic activity. These results indicate that the positively charged, leucine-rich sequence, corresponding to amino acids 141–149 (Leu-Arg-Lys-Leu-Arg-Lys-Arg-Leu-Leu; referred to as LRKLRKRLL in single letter amino acid shorthand; SEQ. ID. No:1) in the mature protein which represents the overlap between the functional peptides identified, is responsible for both the cytostatic and cytotoxic effect. Clay et al., *Biochemistry* 34:11142–51 (1995). When tested against primary neurons in culture, these peptides were also found to elicit degeneration of neurites.

Purified apoE, derived from transfected HEK cells, subjected to thrombin cleavage and separated using gel filtration to collect the 22 kD fragment, yields enhanced toxicity when tested against primary neurons in culture. The 22 kD fragments purified from the E4 isoform is more toxic than E3derived fragments. The putative toxic site is closely associated with one of two well-characterized heparin binding domains associated with residues 141–147 of apoE.

The density of four positively charged amino acid residues in the 141–149 domain clearly make a significant contribution to apoE peptide toxicity. Consistent with this conclusion is the ablation of peptide-mediated toxicity by the polyanionic glycosaminoglycans ("GAG") heparin, heparin sulfate and chondroitin sulfate. However, GAG-binding capacity does not, in itself, account for bioactivity since peptide E211–243, which contains a second heparin-binding site but lacks the 141–149 sequence, is inactive. Furthermore, not all GAGs show inhibition of the toxicity.

While there has been considerable research into the mechanisms underlying Alzheimer's disease, there continues to be an ongoing need for new ways to investigate and combat this disorder and other diseases in which ApoE toxicity has been implicated.

U.S. Pat. No. 4,727,063 discloses low molecular weight heparins having a sulfation degree of at least 2.5 and a molecular weight ranging from 2000 to 9000, prepared by depolymerization and sulfation with a mixture of sulfuric and chlorosulfonic acid. None has a sulfation degree up to 3.5.

U.S. Pat. No. 3,454,560 discloses a process for the depolymerization and sulfabon of chondroitin sulfate by means of sulfuric acid at a concentration not lower than 85% w/w. The sulfuric acid can contain another sulfating agent, such as sulfuric anhydride or chlorosulfonic acid, but the same document specifies that, even operating in said ambient, only sulfuric acid participates in the sulfation reaction.

U.S. Pat. No. 5,508,167, Roses et al., issued Apr. 16, 1996, discloses methods of diagnosing or prognosing Alzheimer's disease in a subject. The methods involve directly or indirectly detecting the presence or absence of an apolipoprotein E type (ApoE4) isoform or DNA, encoding ApoE4 in the subject. The presence of ApoE4 indicates the subject is afflicted with Alzheimer's disease or at risk of developing Alzheimer's disease. A novel immunochemical assay for detecting the presence or absence of the Apolipoprotein E (ApoE) E4 allele in a subject is also disclosed.

U.S. Pat No. 5,384,398, Lormeau et al., issued Jan. 24, 1995, discloses new high molecular mass N,O-sulphated heparosans consisting of chains or of a mixture of chains having a molecular mass of between $1.5 \times 10^4$ and $4.0 \times 10$ D, characterized by a repeating disaccharide structure.

U.S. Pat. No. 5,164,295, Kisilevsky et al., issued Nov. 17, 1992, discloses a method of identifying compounds which impair and/or prevent initiation and/or progression of amyloid deposition, such compounds being useful as therapeutics for treating amyloidosis and amyloid-related disorders.

U.S. Pat. No. 4,956,347, Ban et al., issued Sep. 11, 1990, relates to the use of ATEROID, a mixture of "sulfomucopolysaccharides" comprising heparin, heparan sulfate-like substance, dermatan sulfate, and chondroitin sulfate A and C, for the treatment of patients suffering from Alzheimer's-type senile dementia. ATEROID is defined in the U.S. Pat No. 3,000,787, Bianchini, issued Sep. 19, 1961, as a heparinoid anti-cholesterolemic factor. ATEROID, which is in some aspects similar to heparin, has essentially no anticoagulant effect The patent discloses that ATEROID can be extracted from the small intestine and particularly from the duodenum of mammals, by means of methods suitable for the isolation of aminopolysaccharidic or glycoproteic compounds.

Snow, A. D., et al., *American Journal of Pathology*, Vol. 133, No. Dec. 3, 1988, disclose the presence of heparan sulfate proteoglycan (HSPG) in neuritic plaques associated with Alzheimer's disease. HSPG was detected in the amyloid fibrils present in neuritic plaques in the brains of Alzheimer's patients using antibodies against the protein core of HSPG. Additionally, HSPG was shown to be present in primitive plaques. It is suggested that the accumulation of HSPG in plaques takes place during early stages of plaque development.

Snow, A. D., and Kisilevsky, R., *Laboratory Investigation*, Vol. 53, No. 1, pp. 37–44 (1985), report the temporal relationship between glycosaminoglycan (GAG) accumulation and amyloid deposition during experimental amyloidosis. Using models which facilitate induction of amyloidosis, it was disclosed that amyloid-associated GAGs appear in the tissues together with the AA amyloid protein independent of the tissue type. It is suggested that the appearance of GAG in the inflammatory amyloidosis condition appears to be part of the process involved in the deposition of the AA protein.

Margolis, R. U., and Margolis, R. K., *Neurobiology of Aging*, Vol. 10, pp. 500–502 (1989) disclose various properties of nervous tissue proteoglycans with respect to their proposed relation to amyloid beta-protein in Alzheimer's disease-related amyloidosis. It is pointed out on page 501, column 1, lines 4 to 8 that the role of proteoglycans in Alzheimer's disease amyloidosis is only circumstantial and the role of proteoglycans in it is unclear. At page 502, column 2, lines 3 to 6, it is disclosed that due to the absence of firm evidence specifically linking proteoglycans to pathogenesis of Alzheimer's disease, it is premature to speculate the relationship of proteoglycans to amyloid in degenerative process.

Caputo, C. B., *Neurobiology of Aging*, Vol. 10, pp. 503–504 (1989) refers to the significance of binding of proteoglycans to amyloid. It is disclosed that co-localization of proteoglycans with amyloids indicates that they are binding but the consequence of such binding is unknown. The question is asked of whether proteoglycans bind inadvertently to amyloid or whether the proteoglycans in binding to amyloid or its precursors lead to the formation of beta-pleated sheet conformation or the stabilization of such a conformation. It is suggested that in vitro studies be performed to determine whether Alzheimer amyloid precursor binds to proteoglycans. On page 503, column 1, last paragraph, the possibility that amyloid protein binds well to proteoglycans is raised. However, evidence is referred to which indicates otherwise.

SUMMARY OF THE INVENTION

The present invention relates generally to a method for treating diseases associated with toxicity of Apolipoprotein E ("apoE"). Specifically, the present invention is a new method for treating a mammal having a condition associated with toxicity of whole apolipoprotein E or apoE cleavage fragments containing residues 130–169, comprising administering to said mammal a pharmacologically effective amount of a compound or a pharmaceutically acceptable salt, derivative or fragment thereof which interferes with production of the toxic fragment or interferes with the receptor-binding site associated with residues 130–169 of the apolipoprotein E molecule in said mammal.

In a first embodiment, the pharmacological composition will comprise a glycosaminoglycan or derivative or fragment thereof along with one or more pharmaceutically acceptable carriers, fillers or excipients. The administering step may comprise administering a pharmacological composition comprising an agent selected from the group consisting of heparin, heparan sulfate, dermatan sulfate and fragments thereof along with pharmaceutically acceptable carrier, fillers or excipients. In a second embodiment, the pharmacological composition will comprise a protease inhibitor, or a mixture of protease inhibitors along with one or more pharmaceutically acceptable carriers, fillers or excipients. The administering step may comprise administering a pharmacological composition comprising a protease inhibitor "cocktail" such as a mixture of aprotinin, leupeptin, pepstatin and antipain all available from Sigma Chemical Co. Another embodiment will comprise a combination of the first and second embodiments.

The method may be by oral administration of the interfering compound or a pharmaceutically acceptable salt or derivative thereof into said mammal.

The administering step comprises parenteral administration of the production or receptor-binding site interfering compound or a pharmaceutically acceptable salt or derivative thereof into said mammal. This administration may be by transdermal administration, subcutaneous injection, intravenous injection, intraperitoneal injection, intramuscular injection, intrastemal injection, intrathecal injection, intraventricular and intracerebroventricular injection and infusion techniques.

The methods also comprise administering the interfering compound or a pharmaceutically acceptable salt or derivative thereof along with a lipophilic solvent or carrier. The lipophilic solvent or carrier may be an organic solvent, phosphatidyl choline and cholesterol.

The present method is useful in the treatment of a variety of diseases associated with apoE toxicity including, but not limited to Alzheimer's disease and Alzheimer-related senile dementia, cerebral amyloidosis, coronary artery disease, and atherosclerosis.

Accordingly, an object of the present invention is to provide treating a mammal having a condition associated with toxicity of apolipoprotein E cleavage fragments containing residues 130–169, comprising administering to said mammal, in need of such treatment, a pharmacologically effective amount of compound or a pharmaceutically acceptable salt, derivative or fragment thereof to interfere with generation of toxic fragments containing the receptor-binding site associated with residues 130–169 of the apolipoprotein E molecule in said mammal or to interfere with the receptor-binding site itself.

The present invention has several benefits and advantages. By use of the methods described, a safe and effective treatment may be administered for a variety of diseases associated with apoE toxicity without the toxic side effects associated with many of the treatments available.

Other objects, features and advantages of the present invention will become apparent from the following detailed description. It should be understood, however, that the detailed description and the specific example, while indicating preferred embodiments of the invention, are given by way of illustration only, since various changes and modifications within the scope of the invention will become apparent to those skilled in the art from this detailed description.

DETAILED DESCRIPTION OF THE INVENTION

Apolipoprotein E "apoE", is a constituent of liver-synthesized very low density lipoproteins which function in the transport of triglycerides from the liver to peripheral tissues. It is a recognition site for several cellular lipoprotein receptors, including hepatocyte receptors for chylomicron and VLDL remnants.

The term "apoE receptor-binding side ("ARS"), refers to the binding site contained on the whole apoE protein and the 22 kD fragment and is responsible for binding of apoE with the low density lipoprotein ("LDL") receptor or the LDL receptor-related protein. The apoE receptor binding site is associated with amino acid residues 130 through 169 (Thr-Glu-Glu-Leu-Arg-Val-Arg-Leu-Ala-Ser-His-Leu-Arg-Lys-Leu-Arg-Lys-Arg-Leu-Leu-Arg-Asp-Ala-Asp-Asp-Leu-Gln-Lys-*Arg (Cys)-Leu-Ala-Val-Try-Gln-Ala-Gly-Ala-Arg-Glu-Gly; or as TEELRVRLASHLRKLRKRLLRDADDLQK-*R(C)-LAVYQAGAREG in single letter amino acid shorthand; SEQ. ID. No:2 in the mature protein. The sequence shown occurs in isoforms E3 and E4. The E2 isoform is identical with the exception of a cysteine substitution for arginine at position 158 denoted with an asterisk (SEQ. ID. No:3). The ARS overlaps the apoE heparin-binding site on the apoE protein. The heparin-binding region is a positively charged, leucine-rich sequence, corresponding to amino acids 141–147 (Leu-Arg-Lys-Leu-Arg-Lys-Art-Leu; referred to as RKLRKRL in single letter amino acid shorthand; SEQ. ID. No:4) in the mature protein. ApoE-related proteins lacking these domains are not toxic to neurons.

The 22 kD fragment of the apoE protein is the only major band immunoprecipitated from human brain or CSF samples by a monoclonal antibody that recognizes the putative toxic domain. This fragment runs with an apparent molecular weight of about 22 kD, and likely correspond to the major thrombin cleavage product, which has been shown to be protease-resistant The term "biologically active" refers at least to the ability of a molecule to specifically interfere with the receptor-binding site of apoE ("ARS"), or to interfere with generation of toxic fragments of the apoE molecule having the apoE receptor-binding site, although other general or effector capability may be present in that molecule as well.

Biological activity of an apoE receptor-binding interfering molecule is evidenced by the interference with the binding of apoE with the low density lipoprotein ("LDL") receptor or the LDL receptor-related protein, at least at physiological pH values and ionic strengths. Biological activity of a molecule interfering with generation of toxic fragments is widened by an ability to prevent generation of toxic apoE fragments from full-length apoE.

Preferably, biological activity occurs under biological assay conditions; i.e., those conditions within a pH value range of about 5 to about 9, at ionic strengths such as that of distilled water to that of about one molar sodium chloride, and at temperatures of about 4° C. to about 45° C.

A "derivative" refers to a subject compound having one or more amino acid residues or carbohydrate moieties chemically derivatized by reaction of a functional group. Such derivatized molecules include, for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives.

The term "fragment" refers to any subject compound having a composition less than all of the molecule mentioned herein.

The term "glycosaminoglycan" is a general term for any mucopolysaccharide or sulfomucopolysaccharide. This is a general term for a protein-polysaccharide complex obtained from proteoglycans and containing as much as 95% or more polysaccharide. All the know six classes of glycosaminoglycans contain amounts of glucosamine and galactosamine. This class of compounds includes heparin, heparan sulfate, dermatan sulfate and chondrotin sulfate A and C. Heparin is a mucopolysaccharide comprised of D-glucuronic acid and D-glucosamine, both sulfated, in 1,4-α-linkage, of a molecular weight of from about 6000 D to about 20,000 D. Heparin sulfate, or heparifin sulfate, is an heteropolysaccharide that has the same repeating disaccharide as heparin but with fewer sulfates and more acetyl groups. Dermatan sulfate, or chondroitin sulfate B, is a mucopolysaccharide containing alternating L-iduronic acid and N-acetyl-D-galactosamine 4-sulfate residues. Chondrofflin is a mucopolysaccharide or proteoglycan composed of alternating residues of B-D-glucuronic add and N-acetylgalactosamine sulfate in alternating β1,3 and β1,4 linkages and are present in the ground substance materials in the extracellular matrix of connective tissue. Chondroitin sulfate A has sulfuric residues esterfying the 4-hydroxyl groups of the galactosamine residues. Chondroitin sulfate C contains sulfuric residues esterifying the 6-hydroxyl groups of the galactosamine residues.

The method of the present invention consists of treating a mammal having a condition associated with toxicity of apolipoprotein E cleavage fragments containing residues 130–169, comprising administering to said mammal a pharmacologically effective amount of compound or a pharmaceutically acceptable salt, derivative or fragment thereof to interfere with the generation of toxic fragments of apoE or with the receptor-binding site associated with residues 130–169 of the apolipoprotein E molecule in said mammal.

Amino acid residues 130–169 in human apoE encompass an immunoregulatory domain with both cytostatic and cytotoxic activities against interleukin-2 ("IL2")-dependent T cells. The positively charged, leuvine-rich sequence, corresponding to amino acids 141–149 (Leu-Arg-Lys-Leu-Arg-Lys-Arg-Leu-Leu; referred to as RKLRKRLL in single letter amino acid shorthand; SEQ. ID. No:1) in the mature protein represents the minimum sequence associated with the receptor-binding site ("ARS"), the heparin-binding site, and cytotoxicity. The present method utilizes compounds to interfere with the ARS. While not being bound by theory, it is believed that the interfering compounds will preferably associate temporarily with the binding site and, therefore, block access to the binding site to heparin. The association may be from very weak to very strong, depending on the compound utilized. Alternatively, a compound which forms a covalent bond may be utilized.

The pharmacological composition will preferably comprise a protease inhibitor or a glycosaminoglycan or derivative or fragment hereof along with a pharmaceutically acceptable carrier, fillers or excipients. Protease inhibitors, carriers, fillers and excipients are well known in the art The administering step may comprise administering a pharmacological composition comprising an agent selected from the group consisting of protease inhibitors, heparin, heparan sulfate, dermatan sulfate and fragments thereof along with pharmaceutically acceptable carrier, fillers or excipients.

The methods may be by oral administration of the interfering composition or a pharmaceutically acceptable salt or derivative thereof into said mammal. The methods according to the present invention preferably allow the administration of the interfering molecule in a unitary dose of from about 1 to about 1000 mg. A unitary dose is generally administered from about 1 to about 3 times a day.

The administering step may comprise parenteral administration of the receptor-binding site interfering compound or a pharmaceutically acceptable salt or derivative thereof into said mammal. This administration may be by transdermal administration, subcutaneous injection, intravenous injection, intraperitoneal injection, intramuscular injection, intrasternal injection, intrathecal injection, intracerebroventricular injection and infusion techniques.

The method also comprises administering the interfering compound or a pharmaceutically acceptable salt or derivative thereof along with a lipophilic compound, such as a lipophilic solvent or carrier. The lipophilic solvent or carrier may be an organic solvent, phosphatidyl choline and cholesterol.

The present method is useful in the treatment of a variety of diseases associated with apoE toxicity including, but not limited to Alzheimer's disease and Alzheimer-related senile dementia, cerebral amyloidosis, coronary artery disease, and atherosclerosis. Suitable subjects may include those diagnosed as afflicted with Alzheimer's disease. The present invention may be employed in treating both familial Alzheimer's disease (late onset and early onset) as well as sporadic Alzheimer's disease. Many Alzheimer's disease patients encountered in practice have no obvious family history and have been classified as sporadic. However, genetic factors in early-and late-onset of familial Alzheimer's disease (FAD) are well documented. Late-onset Alzheimers disease is the classification usually used if the disease is diagnosed to occur after the age of 65 in humans.

It is preferred and contemplated that the methods described herein be used in conjunction with clinical diagnostic information known or described in the art which are used in evaluation of subjects with Alzheimer's disease or suspected to be at risk for developing such disease or other apoE-related diseases.

ApoE phenotypes and genotypes are well described and known in the art as described above. The established nomenclature system as well as the phenotypes and genotypes for ApoE, are described in, for example, Zannis et al., *J. Lipid. Res.* 23911 et seq. (1982), which is incorporated by reference herein.

The step of detecting the presence or absence of ApoE4 or of DNA encoding such isoform (including the number of alleles for ApoE4) may be carried out either directly or indirectly by any suitable means and a variety of techniques are known to those skilled in the art. All generally involve the step of collecting a sample of biological material containing either DNA or ApoE from the subject, and then detecting whether or not the subject possesses ApoE4 or DNA encoding such isoform from that sample. For example, the detecting step may be carried out by collecting an ApoE sample from the subject (for example, from cerebrospinal fluid, or any other fluid or tissue containing ApoE), and then determining the presence or absence of an ApoE4 isoform in the ApoE sample (e.g., by-isoelectric focusing or immunoassay).

Studies have shown that apoE fragments ranging from 5 to 22 kD are present in the post-mortem cerebral spinal fluid from both control patients and patients with AD. The only major band immunoprecipitated by a monoclonal antibody that recognizes the putative toxic domain runs with an apparent molecular weight of about 22 kD. This fragment likely corresponds to the major thrombin cleavage product.

Purified apoE, derived from transfected HEK cells, subjected to thrombin cleavage and separated using gel filtration to collect the 22 kD fragment, yields enhanced toxicity when tested against primary neurons in culture. The 22 kD fragments purified from the E4 isoform are more toxic than E3-derived fragments. The putative toxic site is closely associated with one of two well-characterized heparin binding domains associated with residues 141–147 of apoE.

The density of four positively charged amino acid residues in the 141–149 domain clearly make a significant contribution to apoE peptide toxicity. Consistent with this conclusion is the ablation of peptide-mediated toxicity by the polyanionic glycosaminoglycans ("GAG") heparin, heparan sulfate and chondroitin sulfate. Furthermore, not all GAGs show inhibition of toxicity.

The site-interfering compound may be a glycosaminoglycan or derivative or fragment thereof. It is known that glycosaminoglycans are products capable of being obtained by extraction from animal tissues. Certain of these glycosaminoglycans have very advantageous anticoagulating and antithrombotic properties. Typical products of this family are heparin, its cleavage products and their derivatives, as well as heparan sulfate and dermatan sulfate. However, preferred methods of the present invention will utilize compounds without potent anticoagulant properties.

In particular, it is known that dermatan sulfate is a family of polymers with a variable degree of polymerization, formed of repeating units consisting of a uronic acid group (iduronyl or glucuronyl) and of an acetyl 4-sulphated galactosaminyl group (H. W. Stuhlsatz, "The Methodology of Connective Tissue Research", (1976), 137–146). Natural dermatan sulfate has a molecular mass of between $2 \times 10^4$ and $4 \times 10^4$ D. This product is particularly advantageous as an anticoagulant and antithrombin (F. Fernandez et al., British Journal of Haematology, (1986), 64, 309–317). The heparin-binding site interfering compound may be a glycosaminoglycan or derivative or fragment thereof with a molecular mass of between $2 \times 10^1$ and $4 \times 10^5$ D.

It is known that the main heparin chain is constructed in two stages. In a first stage, heparin is biosynthesized from a precursor proteoglycan whose polysaccharide part consists of a family of polymers with a variable degree of polymerization formed from repeating beta -D-glucuronyl-1,4- alpha -N-acetyl-D-glucosaminyl-(1,4) disaccharide units. This polysaccharide part is generally called N-acetylheparosan (J. Navia, Anal. Biochem., (1983), 135, 134–140). This first stage of biosynthesis is the only time when it is truly possible to speak of a "disaccharide unit" because the second stage of the biosynthesis will profoundly change this simple skeleton ("L'heparine, fabrication, structure, proprietes, analyses", J. P. Duelos, (1984) pp. 81–83, Masson Ed.-France).

Natural heparin resulting from biosynthesis is a polysaccharide consisting of molecules of glucuronic acid and of iduronic acid (uronic acids), optionally sulphated in position 2, combined with molecules of glucosamine, optionally sulphated in position 6 and sulphated or acetylated on the amine in position 2. The heparin-binding site interfering compound may be a compound derived from natural heparin.

The natural heparin used as the starting material can be standard heparin or any other commercially available heparin, provided that it has a good quality. A sodium salt of heparin may be used, even if other salts can conveniently be used. It is preferable that starting heparin be anhydrous, hence a preliminary dehydration is properly performed, for example, at a temperature of from about 50° to about 60° C. The interfering compound may be derived from natural heparin through cleavage with enzymes or through other chemical means.

The ARS blocking compound may be, for example, dermatan sulfate (#03125 and #03120), heparan sulfate 1 (#03100), heparan sulfate 4 (#03400), LP heparin fraction (#03010), and HP heparin fraction (#03020) (all from Celsus Laboratories, Inc., Cincinnati, Ohio). Other compounds include heparan sulfate (Product Nos. H5393, H9902, H7640, H9637, and H7641) and heparin (Product Nos. H0880, H8398, and H0878) (all from Sigman Chemical Co., St. Louis, Mo.).

The pharmaceutical compositions of the present invention can be formulated for the oral, sublingual, subcutaneous, intravenous, transdermic or rectal administrations in dosage units and in admixture with pharmaceutical excipients or vehicles. Convenient dosage forms include, among those for oral administration, tablets, powders, granulates, and, among those for parenteral administration, solutions especially for transdermal administration, subcutaneous injection, intravenous injection, intraperitoneal injection, intramuscular injection, intrastemal injection, intrathecal injection and infusion techniques.

The pharmaceutical compositions of the present invention are administered, in the above mentioned forms and routes, to animals and man in case of a pathological increase in toxicity of apoE fragments containing the residue sequence 130–169, particularly in the treatment of Alzheimer's disease.

The daily amount in the aforesaid indications may range from 0.1 to 100 mg/kg and each unitary dose may contain from 1 to 1000 mg of the active ingredient. Such unitary dose can be administered from 1 to 3 times a day for the treatment of dementia disorders and atherosclerosis.

The dosage can vary widely as a function of the age, weight and state of health of the patient, the nature and the severity of the ailment, as well as of the administration route. These doses can naturally be adjusted for each patient according to the results observed and the blood analyses previously carried out.

The following examples illustrate and explain the present invention but should not be taken as limiting the present invention in any regard.

EXAMPLE 1

Since the 22 kD fragment contains the domain associated with toxicity and corresponds to the major N-terminal proteolytic fragment of apoE, assessment of the efficacy of a compound can first be screened by measuring the inhibition of the 22 kD toxicity in vitro. The 22 kD thrombolytic cleavage fragment product of apoE is neurotoxic and is purified from medium of HEK cells transfected with the gene for human apoE4. Neuronal toxicity is then assessed using dissociated embryonic chick sympathetic neurons in 96 well microtiter plates. Following the addition of the fragments, the cultures are incubated overnight Viability is then assessed by vital dye staining.

EXAMPLE 2

Effects of apoE 22 kDa Peptides on Sympathetic Neurons in Culture.

Transfected HEK cells are cultured as previously described (LaDu, M. J., et el., *J. Biol. Chem.* 258:12348–54 (1983).) The apoE is concentrated from conditioned medium by ultfiltration (10 kDa cut-off membrane, Amicon) followed by heparin column chromatography (heparincoupled agarose beads, Sigma). The purified apoE is then digested with thrombin and the resulting fragments are separated by HPLC gel filtration chromatography (Bio SEC-Bio Rad). After buffer exchange with centricon 10 (Amicon) and lyophilization, the purified 22 kDa fragment is subjected to amino acid analysis. For neurotoxicity studies, lumbar sympathetic chain ganglia are isolated from embryonic day nine chicken embryos (Spafas, Inc., Roanoke, Ill.) under sterile conditions in unsupplemented Ham's F12 medium (Sigma). The dissected chains are exposed to trypsin (0.25%) for 20 minutes at 37° C. The trypsin is inactivated by adding fetal bovine serum. The chains are washed three times with medium and then triturated with flamed Pasteur pipettes to dissociate the cells. The cells are resuspended in Neurobasal medium (Gibco) and plated into 96-well plates pretreated with poly-ornithine. Dishes are incubated at 37° C. with 5% $CO_2$/95% air. Following overnight incubation, the cells are treated with dermatan sulfate (#03125), Celsus Laboratories, Inc., Cincinnati, Ohio), diluted in F12 medium supplemented with 100 $\mu$M putrescine, 20 nM progesterone, 100 $\mu$g/ml human transferrin, 30 nM selenium and 1% antibiotics (penicillin-streptomycin). The average molecular weight is approximately 35 kD. The neuronal cells are pre-incubated for 10 min. at 37° C. with 4 $\mu$M of the dermatan sulfate. The toxic fragments are added to the culture medium. Controls use the corresponding vehicle. After overnight incubation, the cells are labeled with a vital dye (5-carboxyfluorescein diacetate, acetoxymethyl ester, Molecular Probes, Eugene, Oreg.) for 30 minutes. The wells are washed with fresh F12 medium and images of the stained cells are collected from each well by using a Diaphot inverted fluorescence microscope connected to a Macintosh IIfx computer equipped with a Framegrabber video card. The number of labeled neurons is quantified from the stored images with NIH Image software (version 1.57). The results show the number of cells surviving following overnight exposure to different concentrations of either the E3 or E4derived 22 kDa fragment. Those treated with the dermatan sulfate show toxicity is completed abated.

EXAMPLE 3

Same as above only neuronal toxicity is tested with heparan sulfate (#03105, Celsus Laboratories, Inc., Cincinnati, Ohio).

EXAMPLE 4

Same as above only neuronal toxicity is tested with the high potency heparan fraction (#03025, Celsus Laboratories, Inc., Cincinnati, Ohio).

EXAMPLE 5

Results of in vitro experiments showing interference effect of a protease inhibitor mixture.

Full-length apoE4 (8 $\mu$M) was added to primary chick sympathetic neurons in cultures using the procedure of Example 1 in the presence and absence of a mixture of protease inhibitors obtained from Sigma Chemical Co.:

| protease inhibitor | concentration |
| --- | --- |
| aprotinin | 1.5 ± 0.5 $\mu$g/ml |
| leupeptin | 1.5 ± 0.5 $\mu$g/ml |
| pepstatin A | 1.5 ± 0.5 $\mu$g/ml |
| antipain | 1.5 ± 0.5 $\mu$g/ml |

The protease inhibitor mixture was found to significantly reduce the toxicity of the apoE and to reduce the production of apoE fragments (based on Western blotting). The same protease inhibition mixture did not block the toxicity of the apoE fragment or the long tandem apoE peptide. Therefore, the method of interfering is likely not due to interfering with the binding of apoE fragments to the receptor, but due to prevention of generation of toxic fragments.

What is claimed is:

1. A method of treating conditions associated with apolipoprotein E toxicity, comprising administering a composition comprising a pharmacologically effective amount of an interfering molecule capable of interfering with neural toxicity of fragments of apolipoprotein E containing the 130–169 amino acid residues wherein the fragments have a molecular weight of at least 5kD.

2. A method according to claim 1 wherein the interfering molecule interferes with a receptor-binding site of the apolipoprotein E associated with amino acid residues 130 through 169.

3. A method according to claim 2 wherein the receptor-binding site of the apolipoprotein E binds low density lipoprotein receptor-related proteins.

4. A method according to claim 1 wherein the interfering molecule is selected from the group consisting of: protease inhibitors, glycosaminoglycans, glycosaminoglycan salts, substituted glycosaminoglycans, glycosaminoglycan fragments, and mixtures thereof.

5. A method according to claim 2 wherein the interfering molecule is selected from the group consisting of substituted and unsubstituted heparin, and fragments and pharmaceutically acceptable salts thereof; substituted and unsubstituted dermatan sulfate, and fragments and pharmaceutically acceptable salts thereof; substituted and unsubstituted chondroitin sulfate A, and fragments and pharmaceutically acceptable salts thereof; substituted and unsubstituted chondroitin sulfate C, and fragments and pharmaceutically acceptable salts thereof, and mixtures thereof.

6. A method according to claim 2 wherein the composition further comprises at least one ingredient selected from the group consisting of carriers, fillers, and excipients.

7. A method according to claim 2 wherein the composition further comprises a lipophilic compound.

8. A method according to claim 5 wherein the lipophilic compound is selected from the group consisting of organic solvents, phosphatidyl choline, cholesterol and mixtures thereof.

9. A method according to claim 1 wherein the administering comprises oral administering.

10. A method according to claim I wherein the administering comprises parenteral administering.

11. A method according to claim 10 wherein the administering is a dosing method selected from the group consisting of transdermal administering, subcutaneous injecting, intravenous injecting, intraperitoneal injecting, intramuscular injecting, intrastemal injecting, intrathecal injecting, intraventricular injecting, intracerebroventricular injecting, and infusing.

12. A method according to claim 2 wherein the interfering molecule is administered in a unitary dose of from about 1 to about 1000 mg.

13. A method according to claim 12 wherein the unitary dose is administered from about 1 to about 3 times a day.

14. A method according to claim 1 wherein the condition is Alzheimer's disease.

15. A method according to claim 1 wherein the condition is Alzheimer's-type senile dementia.

16. A method of treating conditions associated with apolipoprotein E toxicity, comprising the steps of obtaining a biological sample from a subject, assaying the sample for the presence of apolipoprotein E, administering to the subject a composition comprising a pharmacologically effective amount of a receptor-binding interfering molecule, said interfering molecule being capable of interfering with a receptor-binding site of the apolipoprotein E associated with amino acid residues 130 through 169.

17. A method according to claim 16 wherein the biological sample is cerebrospinal fluid.

18. A method according to claim 16 wherein the apolipoprotein E is isoform apolipoprotein E4.

19. A method of treating Alzheimer's disease, comprising the steps of:

(a) obtaining a cerebrospinal fluid sample from a subject, (b) assaying the sample for the presence of apolipoprotein E4, and (c) administering from about 1 to about 3 times a day a receptor-binding interfering molecule in a unitary dose of from about 1 to about 1000 mg; wherein the receptor-binding interfering molecule is selected from the group consisting of glycosaminoglycans, glycosaminoglycan salts, glycosaminoglycan derivatives, glycosaminoglycan fragments, and mixtures thereof.

20. A method according to claim 1 wherein the interfering molecule is a protease inhibitor.

* * * * *

SEQUENCE LISTING

<160> NUMBER OF SEQ ID NOS: 4

<210> SEQ ID NO: 1
<211> LENGTH: 9
<212> TYPE: PRT
<213> ORGANISM: Homo sapiens

<400> SEQUENCE: 1

Leu Arg Lys Leu Arg Lys Arg Leu Leu
 1               5

```
<210> SEQ ID NO: 2
<211> LENGTH: 40
<212> TYPE: PRT
<213> ORGANISM: Homo sapiens

<400> SEQUENCE: 2

Thr Glu Glu Leu Arg Val Arg Leu Ala Ser His Leu Arg Lys Leu Arg
 1               5                  10                  15

Lys Arg Leu Leu Arg Asp Ala Asp Asp Leu Gln Lys Arg Leu Ala Val
             20                  25                  30

Tyr Gln Ala Gly Ala Arg Glu Gly
         35                  40

<210> SEQ ID NO: 3
<211> LENGTH: 40
<212> TYPE: PRT
<213> ORGANISM: Homo sapiens

<400> SEQUENCE: 3

Thr Glu Glu Leu Arg Val Arg Leu Ala Ser His Leu Arg Lys Leu Arg
 1               5                  10                  15

Lys Arg Leu Leu Arg Asp Ala Asp Asp Leu Gln Lys Cys Leu Ala Val
             20                  25                  30

Tyr Gln Ala Gly Ala Arg Glu Gly
         35                  40

<210> SEQ ID NO: 4
<211> LENGTH: 7
<212> TYPE: PRT
<213> ORGANISM: Homo sapiens

<400> SEQUENCE: 4

Leu Arg Lys Leu Arg Lys Arg
 1               5
```